United States Patent

Marinello

[19]

[11] Patent Number: 5,771,898

[45] Date of Patent: Jun. 30, 1998

[54] METHOD AND APPARATUS FOR ACCURATE COUNTING OF PACED HEARTBEATS

[75] Inventor: Stephen A. Marinello, Beverly, Mass.

[73] Assignee: Siemens Medical Systems, Inc., Iselin, N.J.

[21] Appl. No.: 770,034

[22] Filed: Dec. 19, 1996

[51] Int. Cl.[6] .................................................. A61B 5/0456
[52] U.S. Cl. .......................... 128/697; 128/706; 128/901
[58] Field of Search .................................... 128/696, 697, 128/702, 706, 707, 901

[56] References Cited

U.S. PATENT DOCUMENTS

| | | | |
|---|---|---|---|
| 4,674,509 | 6/1987 | DeCote, Jr. ............................... | 128/697 |
| 4,893,632 | 1/1990 | Armington ............................... | 128/696 |
| 4,934,376 | 6/1990 | Armington ............................... | 128/697 |
| 5,033,473 | 7/1991 | Wang et al. .............................. | 128/696 |
| 5,381,803 | 1/1995 | Herleikson et al. ..................... | 128/708 |
| 5,540,232 | 7/1996 | Laney et al. ............................. | 128/697 |
| 5,660,184 | 8/1997 | Donehou et al. ........................ | 128/696 |

*Primary Examiner*—Jeffrey R. Jastrzab
*Attorney, Agent, or Firm*—Lawrence C. Edelman

[57] ABSTRACT

A heartrate monitor of the invention includes a signal receiver adapted for being coupled to at least one sensor coupled to a medical patient, for providing an ECG signal and a pacemaker detection signal. A pacemaker activity checker, responsive to the pacemaker detection signal and the ECG signal provides first and second output signals, the first output signal indicating the occurrence of a QRS complex in the vicinity of the pacemaker detection signal, and the second output signal indicating the occurrence of an overshoot in the vicinity of the pacemaker detection signal. An overshoot validator, responsive to the ECG signals and the second output signal indicates the validity of the indicated overshoot. A QRS detector, responsive to the ECG signal, indicates the occurrence of a QRS complex in the ECG signal. A logic combining means, responsive to at least the first output signal, the output of the overshoot validator and the output of the QRS detector, determines a combined QRS detection signal, that accurately indicates the occurrence of QRS's. A heartrate determining means responsive to the combined QRS detection signal provides an accurate indication of the heartrate for the medical patient.

6 Claims, 6 Drawing Sheets

METHOD AND APPARATUS FOR ACCURATE COUNTING OF PACED HEARTBEATS

BACKGROUND OF THE INVENTION

1. Field of the Invention

The present invention relates generally to heartbeat monitoring, and in particular to accurate monitoring of QRS complexs in the presence of pacemaker pulses.

2. Description of the Background Art

ECG (electrocardiogram) monitors attempt to compute and indicate, generally in a real-time manner, the heart rate of a patient, as well as other parameters indicative of the patient's health, such as a body temperature, blood pressure, etc. Computation of heart rate for a patient having an artificial pacemaker is complicated by the presence of artificial pacemaker pulses in the patient's ECG signal, which may or may not be correlated in time with the patient's cardiac response, i.e., the QRS complex. These artificial pacemaker pulses may be erroneously counted as QRS complexes, resulting in an indication of inaccurately high heart rates, or worse yet, a heart rate when in fact there is none. Additionally, artificial pacemaker pulses may have overshoot or undershoot, an exponentially decaying electrical signal following the pacemaker pulse which is caused by capacitive elements in the pacemaker-skin-electrode system. These overshoots or undershoots may also be erroneously interpreted as valid QRS complexes, again resulting in computation and indication of inaccurately high heart rates.

In addition to false QRS detections (detections of pacemaker pulses as QRS complexes), situations arise which may cause a monitor to fail to detect valid paced QRS complexes (i.e., QRS complexes resulting from pacemaker pulses applied to the heart), resulting in an indication of an inaccurately low heart rate, or even an indication of asystole, a condition of no detected heart beats. Such situations occur when:

QRS complexes are buried in an pacemaker's overshoot or undershoot, causing the QRS to be not detected by certain systems which have been designed to avoid detection during pacemaker overshoot or undershoot, Valid (real) QRS complexes which follow a pacemaker pulse are detected, but misclassified by certain systems as overshoot or undershoot, with the result that valid complexes are rejected, and ECG signals are distorted when electronically acquired and amplified by an ECG monitor, especially due to 'ringing', an exponentially decaying sinusoidal response due to a large amplitude pacemaker pulse passing through a notch filter intended to remove line-frequency interference. Since this ringing may appear to certain monitor systems as valid QRS complexes, such monitor systems are designed to not detect QRS's during ringing, resulting in a monitor system which has diminished sensitivity to QRS complexes and consequent non-detection of low-level QRS complexes.

It is known that some prior art heart rate monitors have employed techniques which search for QRS complexes in the vicinity of a detected pacemaker pulse. However, these systems did not simultaneously solve all of the above-mentioned problems of fused beats (QRS complexes that occur at nearly the same time as pacemaker pulses), overshoot or undershoot, small coupling intervals, pacemaker-non-capture beats, and low amplitude or small width QRS complexes.

Some systems were unsatisfactory primarily because they employed blanking periods to prevent false positive QRS detections (falsely indicating a QRS detection when in fact there is no QRS) as a result of pacemaker pulse overshoot or undershoot. However, the use of blanking periods undesirably caused false negative detections (falsely not indicating a detection) of many valid QRS complexes that resulted from the pacemaker pulses. Other systems did not employ blanking periods, but detection capability of the system was purposely diminished (desensitized), to the point that it could no longer distinguish ringing artifact from a low-amplitude QRS complex.

Thus, in general, previous systems were either:

1) Sensitive to QRS complexes, but falsely detected QRS complexes during overshoot or undershoot, or 2) Insensitive to overshoot or undershoot, but also insensitive to detection of certain QRS complexes.

Since false detection during overshoot or undershoot is the more serious problem (an actual patient asystole might go undetected), most current art systems are designed to work with the second set of trade-offs. This means that many false low heartrate and asystole indications can be expected.

It is an object of the present invention to solve the problem of inaccurate heart rate indications in the presence of pacemaker pulses.

SUMMARY OF THE INVENTION

The present invention solves the problems of inaccurate indications of paced heart rates by providing an accurate indication of the presence or absence of a QRS complex in the vicinity of each detected pacemaker pulse. This way, a heartrate monitor using the invention is able to avoid false detections of QRS complexes while also providing sensitive detection of paced QRS complexes. This is primarily obtained by being able to reject sensed pacer overshoot and undershoot, while also being sensitive to many more QRS complexes.

More specifically, the heartrate monitor of the invention includes a signal receiver adapted for being coupled to at least one sensor coupled to a medical patient, for providing an ECG signal and a pacemaker detection signal. A pacemaker activity checker, responsive to the pacemaker detection signal and the ECG signal provides first and second output signals, the first output signal indicating the occurrence of a QRS complex in the vicinity of the pacemaker detection signal, and the second output signal indicating the occurrence of an overshoot in the vicinity of the pacemaker detection signal. An overshoot validator, responsive to the ECG signals and the second output signal indicates the validity of the indicated overshoot. A QRS detector, responsive to the ECG signal, indicates the occurrence of a QRS complex in the ECG signal. A logic combining means, responsive to at least the first output signal, the output of the overshoot validator and the output of the QRS detector, determines a combined QRS detection signal, that accurately indicates the occurrence of QRS's. A heartrate determining means responsive to the combined QRS detection signal provides an accurate indication of the heartrate for the medical patient.

DETAILED DESCRIPTION OF THE PREFERRED EMBODIMENTS

Figure 1:
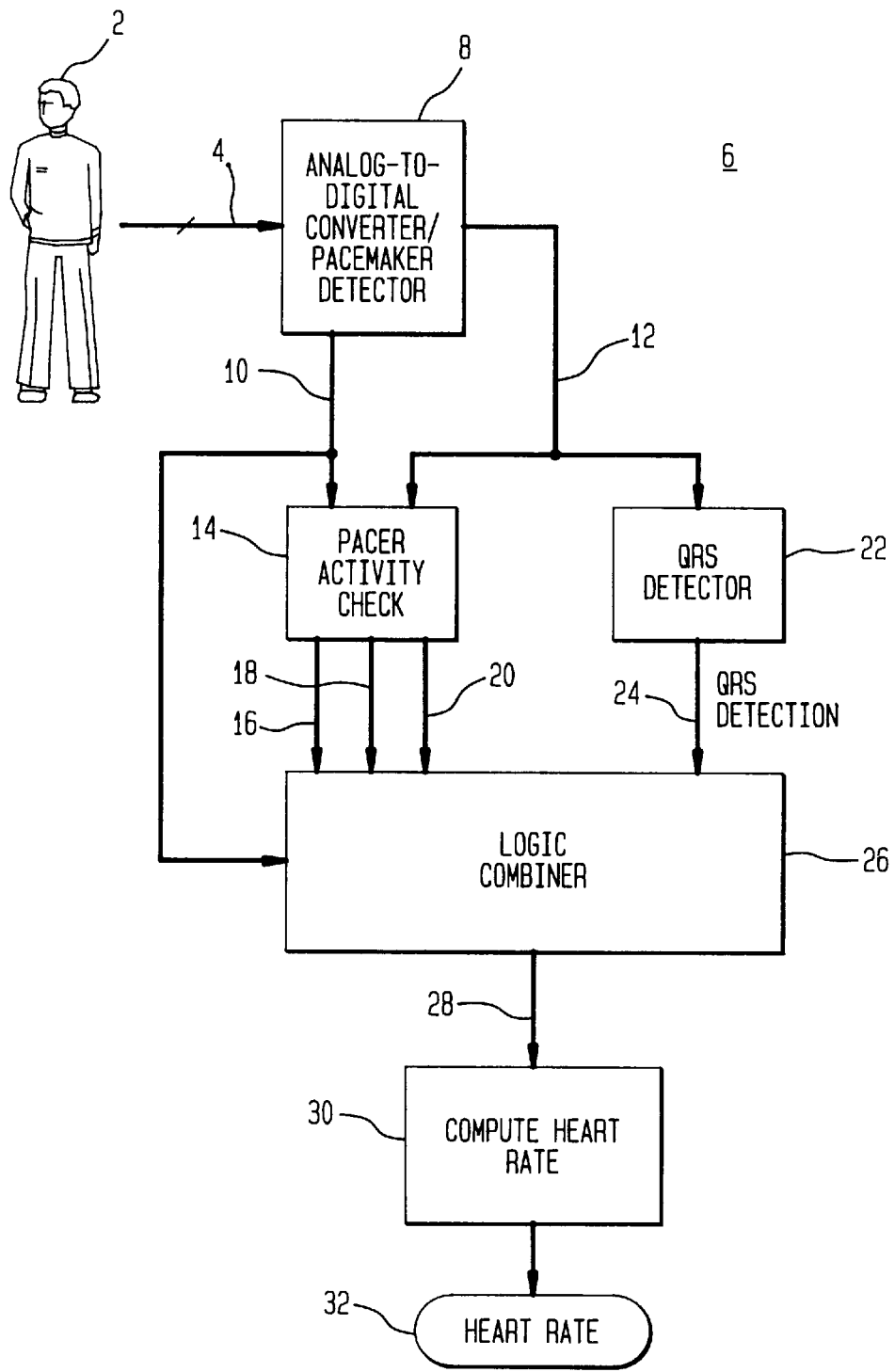
FIG. 1 illustrates in block diagram form a heart rate monitor constructed in accordance with the principles of the present invention.

An overview of the pacemaker processing system is shown in FIG. 1. A patient 2 is connected to plurality of body surface electrodes 4 which sense surface electrical potentials of the patient and carry an electrical representation of the patient's ECG to a heart rate monitor 6. In monitor 6 the ECG signal is applied to a signal receiver, typically called a front-end signal processor of conventional design, that includes an analog-to-digital converter/pacemaker detector 8. The analog-to-digital converter/pacemaker detector 8 is of conventional design (and may be embodied in either hardware or software, as is true with the remainder of the signal processing to be described) and produces 2 outputs: a logical signal (True or False) pacemaker pulse detection signal 10 (using e.g., a slew rate detector technique), which is True when an artificial pacemaker spike has been detected and False otherwise; and a plurality of digital ECG signals 12, each representative of a corresponding one of the ECG signals sensed by electrodes 4.

A pacer activity checker 14 is responsive to the pacemaker pulse detection signal 10 and the digital ECG signal 12, for producing, in a preferred embodiment of the invention, three logical output signals: a pre-pace pulse QRS detection signal 16, which is True if a QRS has been detected by the pacer activity checker 14 in a given time window before the indication of a pacemaker pulse by the pacemaker pulse detection signal 10, and False otherwise; a post-pace pulse QRS detection signal 18, which is True if a QRS has been detected by the pacer activity checker 14 in a given time window after the indication of a pacemaker pulse by the pacemaker pulse detection signal 10, and False otherwise; and an overshoot detection signal 20, which is True if a pacemaker overshoot or undershoot has been detected by pacer activity checker 14 in the vicinity of a pacemaker pulse as indicated by the pacemaker pulse detection signal 10, and False otherwise. In an alternative embodiment, pacer activity checker 14 may only provide post-pace QRS detection signal 18 and not pre-pace QRS detection signal 16, and still obtain a QRS indicator that is more accurate than known in the prior art.

A QRS detector 22 of conventional design, such as an amplitude detector, operates in parallel with (i.e., in addition to) the pacer activity checker 14. QRS detector 22 is responsive to the digital ECG Signal 12 and produces as an output a logical QRS detection signal 24, which is True if a QRS has been detected by detector 22, and False otherwise. Alternatively, detector 22 may comprise the apparatus shown in an application by the same assignee, filed on Dec. 16, 1996 entitled METHOD AND APPARATUS FOR USING MULTIPLE LEADS FOR QRS DETECTION.

In accordance with the principles of the present invention, a logic combiner 26 is responsive to the pacemaker pulse detection signal 10, paced QRS detection signals 16 and 18 (or just 16 in an alternative embodiment), overshoot detection signal 20 and QRS detection signal 24 for producing a combined QRS detection signal 28, which is true (indicating a detected QRS) when the logic combiner 26 has determined that a paced or non-paced QRS complex is present, and False otherwise, irrespective of the output of QRS detector 22. For proper operation of the invention, it does not matter if logic combiner 26 actually inhibits or passes indications of QRS's detected by detector 22 from appearing in the combined QRS detection signal 28, or if logic combiner internally generates such indications of QRS detections based upon its input signals.

In the preferred embodiment the above input signals are combined in accordance with the following truth table:

| Overshoot signal 20 | Pre-pacer signal 16 | Post-pacer signal 18 | Action on QRS's from Detector 22 |
| --- | --- | --- | --- |
| True | False | False | Inhibit QRS |
| True | True | False | Count QRS as paced QRS if dual-chamber |
| False | True | False | Count QRS as paced QRS if dual-chamber |
| True | False | True | Count QRS as paced QRS |
| False | False | True | Count QRS as non-paced QRS |
| False | False | False | Count QRS as non-paced QRS |

Thus, as indicated by the first row of the above table, logic combiner 26 inhibits passage of QRS detections from QRS detector 22 in the case where the overshoot signal 20=True and the post-pacer QRS signal 18=False (i.e., there is overshoot present and no post-pace QRS, so any indication by detector 22 of a detected QRS is probably really a detection of the overshoot and not a valid QRS). Furthermore, if overshoot signal 20=True and post-pacer QRS signal 18=True, as shown by the fourth row of the above table, then a paced QRS is indicated as being detected regardless of the output of QRS detector 22. A paced QRS complex is defined as a QRS complex occuring within 250 msec. after a pacemaker pulse. Logic combiner 26 can make this calculation since it has pacemaker pulse signal 10 as an input.

If a pre-pacer QRS indication has been determined by pacer activity checker 14 (the second and third rows of the above table), then any QRS detections indicted by detector 22 are counted (indicted in output signal 28), provided a dual-chamber pacemaker is not in use. Detection of a dual-chamber pacemaker is made by measuring the interval between pacemaker pulses: if the interval is smaller than a threshold, then a dual-chamber pacemaker is detected. Again, such measurement can be made in logic combiner 26.

If a pacemaker pulse is detected within a given time period surrounding a QRS detection indicated by QRS detector 22, then the QRS is labeled as a paced QRS; otherwise it is labeled as a non-paced QRS. Any QRS detections from pacer activity checker 14 that are validated by logic combiner 26, e.g., those shown by rows 2–4 of the above table, are labeled as paced QRS complexes.

A heart rate computer 30 computes the patent's heart rate 32 over a given time period, using well known techniques, using the combined QRS detection signal 28 from logic combiner 26 for providing to a user of monitor 6 an indication 32, which may be one or more of a visual display (numeric and/or blinking icon), audible alarm, as well as other uses of the information, such as trending and remote monitoring. Note, although processing for only a single ECG signal is described, multiple ECG signals could be processed in accordance with the embodiment shown in FIG. 7, further improving the accuracy of the described heart rate monitor.

Figure 2:
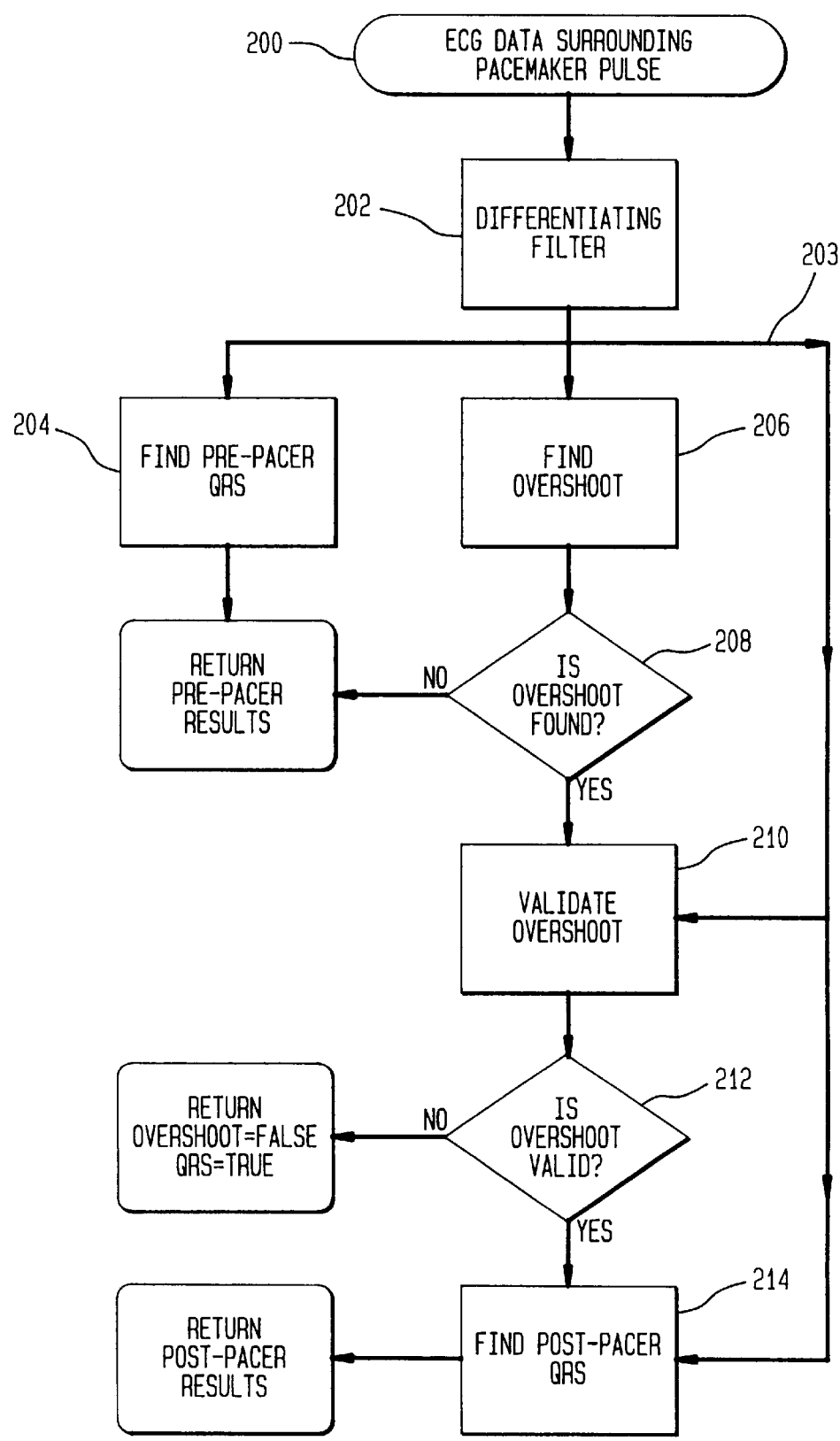
FIG. 2 illustrates a flow diagram of the pacer activity checker shown in FIG. 1.

FIG. 2 illustrates a flow diagram of a preferred embodiment for the pacer activity checker 14 of the invention. An overview of pacer activity checker 14 follows. In step 200, ECG data that surrounds a detected pacemaker pulse from a single ECG signal is passed through a differentiating filter step 202. Differentiation of the ECG data enables activity detection by relatively simple amplitude threshold excursion techniques. The filtered ECG data 203 is passed to a find pre-pacer QRS step 204, which causes pre-paced QRS detection signal 16 to be True if a QRS is detected before the pacemaker spike, and False otherwise; and to a find overshoot step 206 which causes overshoot detection signal 20 to be True if overshoot is found, and False otherwise. At step 208, if overshoot is not found, the results of find pre-pacer QRS step 204, True or False, are passed from pacer activity checker 14 to logic combiner 26.

If step 208 finds overshoot, then the overshoot is validated by a validate overshoot step 210. This step provides a Yes (True) if the overshoot is valid, and a No (False) otherwise. If the overshoot is true, then step 212 causes find post-pacer QRS step 214 to be invoked, and the results, True if a QRS is found, False otherwise, are passed from pacer activity checker 14 to logic combiner 26.

Thus, the pacer activity checker of the invention will attempt to find an overshoot before supplying the pre-pacer QRS detection signal 16. This allows certain dual-chamber pacemaker signals with overshoots, but without QRS complexes, to be correctly rejected (not indicated as a QRS complex) by the activity checker of the invention. Furthermore, validate overshoot step 210 allows more accurate detection of QRS complexes as compared with the prior art by preventing QRS complexes from being falsely classified as overshoots. Such a false classification of overshoot would cause the post-pacer QRS search to start looking for the QRS after the QRS has already passed. Such prior art techniques would therefore indicate asytole for these waveforms which contained QRS complexes and pacemaker pulses without overshoot, while the technique of the present invention is able to properly detect such QRS complexes.

Details of the processes in pacer activity checker 14 will be described next.

Figure 3:
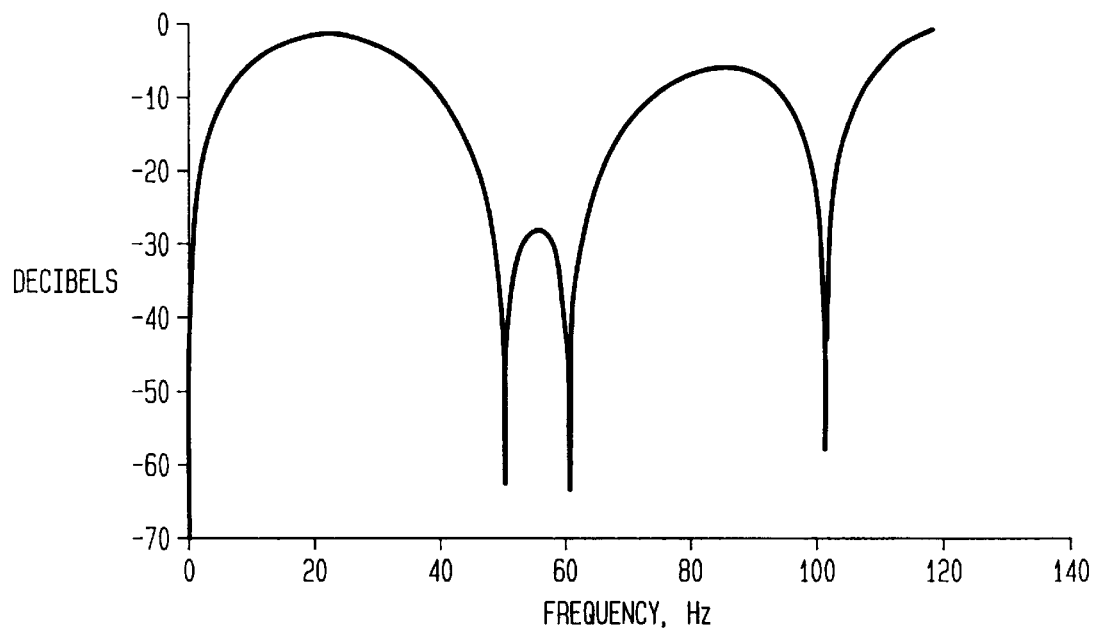
FIG. 3 illustrates a frequency response plot of a differentiating filter shown in FIG. 2.

The differentiating filter step 202 may be embodied by a digital FIR filter which conditions the ECG data by removing ringing caused by notch filters which are used to remove 50 Hz or 60 Hz line-frequency interference. In a preferred embodiment, the invention uses the FIR filter $H(z)= 0.5-0.0625z^{-1} +0.5z^{-2} -0.5z^{-5} +0.0625z^{-6} -0.5z_{-7}$. Filter step 202 also differentiates the ECG signal from frequencies of 0 to 20 Hz, frequencies from 20 to 60 Hz are attenuated, and frequencies above 60 Hz have been removed by processing in the front-end of monitor 6. A frequency response plot of the filter is shown in FIG. 3. This filter is able to remove notch filter ringing from both the 60 Hz and 50 Hz notch filters, and is superior to prior art techniques in that it allows QRS complexes to be found following a pacemaker pulse with or without an overshoot.

Figure 5A:
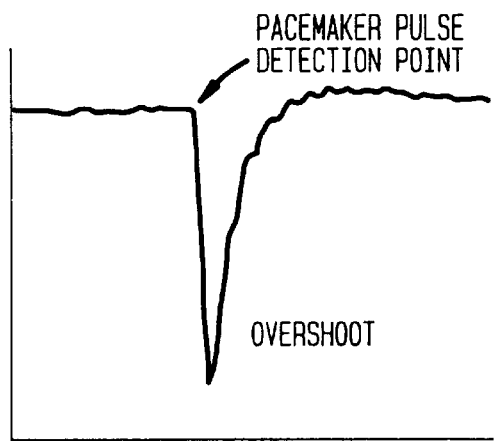
FIGS. 5a–5f illustrate the effect of the differentiating filter on ECG data.
Figure 5B:
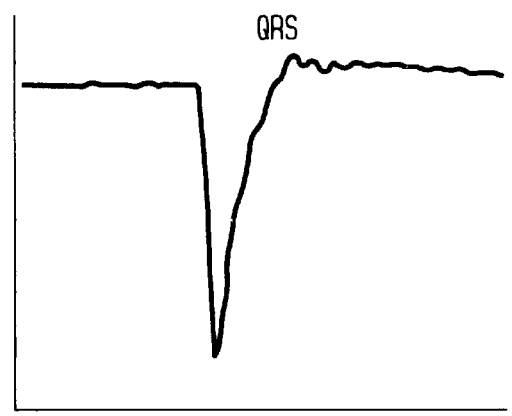

FIGS. 5a –5e illustrate the effect of differentiating filter step 202 on ECG data. Example pacemaker signals may be seen in FIGS. 5a and 5b. FIG. 5a shows a pacemaker overshoot; and FIG. 5b shows a pacemaker overshoot with an associated QRS. Notice in either case the 'ringing' which appears as small sinusoidal waves following the overshoot.

Figure 5C:
Figure 5D:

FIGS. 5c and 5d show the ECG waveforms of FIGS. 5a and 5b after filtering in accordance with the prior art filter, such as a first difference FIR filter of the type $H(z)=1-z^{-1}$. Notice how the 'ringing' is of larger amplitude than before filtering, and how the presence of the QRS complex in FIG. 5d is masked by the ringing.

Figure 5E:
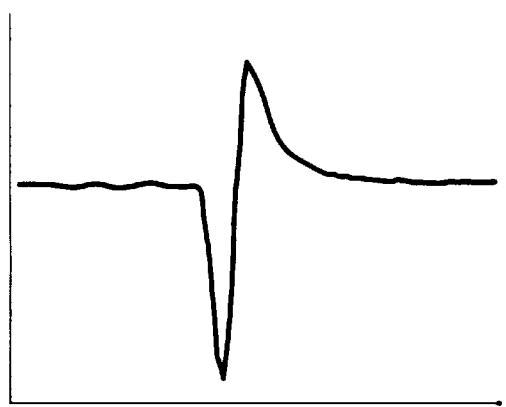
Figure 5F:
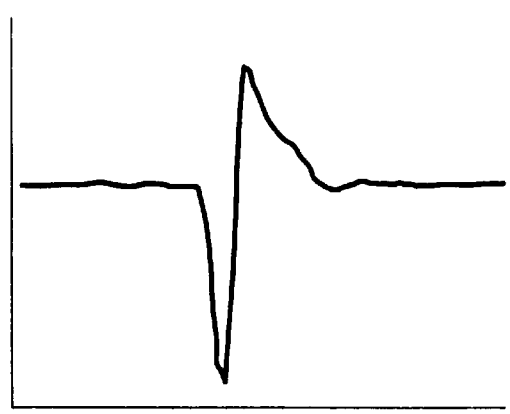

FIGS. 5e and 5f show the ECG waveforms of FIGS. 5a and 5b after filtering in accordance with differentiating filter step 202. Notice how the ringing is not present in FIG. 5e, and how the QRS complex is distinct in FIG. 5f.

The find pre-pacer QRS step 204, counts in the 100 ms preceding a pacemaker pulse, the number of filtered ECG samples having an amplitude which is greater than a positive threshold level (i.e., 0.06 mv), as well as the number which are smaller than a negative threshold (0.06 mV). If the absolute value of the difference of the 2 counts exceeds a threshold count (i.e., a count of 5 samples), then pre-pacer activity is "tentatively" detected. Additionally, if the sum of the absolute values of the filtered ECG samples in the 100 ms preceding a pacemaker pulse exceeds a given threshold (0.875 mV), then pre-pacer activity is "tentatively" detected.

Pre-pacer activity is only "tentatively" detected, since a pre-pacer QRS is only indicated as TRUE if the post-pacer activity is indicated as FALSE. Physiologically, both pre- and post-pacer QRS's are not possible.

The find overshoot step 206 determines if an overshoot is present by looking in a time region (e.g., 400 ms) just after a pacemaker pulse for an amplitude excursion in the filtered ECG samples which exceeds a positive or negative threshold of, e.g., +0.125 mV, or –0.125 mV, respectively. If either of the aforementioned thresholds are exceeded, then overshoot is detected; otherwise, overshoot is not detected.

Figure 4:
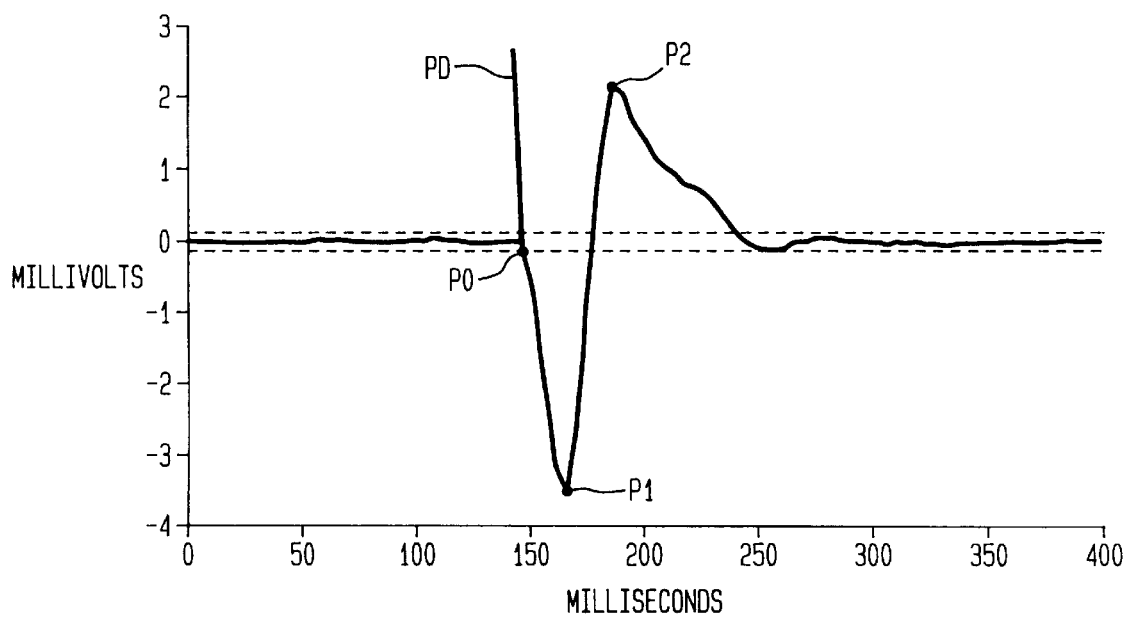
FIG. 4 illustrates an examplary waveform of a filtered pacer overshoot having a QRS complex.

The validate overshoot step 210 determines if a detected overshoot is a valid overshoot or a QRS complex, by performing operations on the filtered ECG samples. Referring to FIG. 4, which shows an example of a filtered pacer overshoot having a QRS complex:

1. Label the point after the detected pacemaker pulse $P_D$ at which overshoot is first detected as 'P0'.
2. Locate a point 'P1' by searching for a point later in time than 'P0' which is a peak. A peak is defined as the sample whose following sample is smaller in amplitude if the amplitude at 'P0' is positively signed, or as the sample whose following sample is larger in amplitude if the amplitude at 'P0' is negatively signed.
3. If the point 'P1' is not found by the aforementioned method, then a QRS is not detected, and overshoot is detected. This is because a signal without an identifiable 'P1' does not match the expected morphology of a QRS complex, and so must be an overshoot.
4. Locate a point 'P2' by searching for a point later in time than 'P1' which is a peak. A peak is defined as the sample whose following sample is larger in amplitude if the amplitude at 'P1' is positively signed, or as the sample whose following sample is smaller in amplitude if the amplitude at 'P1' is negatively signed.
5. If the point 'P2' is not found, then a QRS is detected and overshoot is not detected. This is because a signal without an identifiable 'P2' does not match the expected morphology of an overshoot, and so must be a QRS complex.

6. Finally, the following computation is made:

$$R = \frac{ECG_{P2}}{ECG_{P1}}$$

Thus, R is the sample voltage at point 'P2' divided by the sample voltage at point 'P1'. If R exceeds a given threshold (i.e., 0.781), then a QRS is detected and overshoot is not detected; otherwise a QRS is not detected, and overshoot is detected. This is because a valid overshoot's 'P2' sample voltage must be significantly smaller than its 'P1' sample voltage since valid overshoots have a exponentially decaying morphology, and therefore the slope decreases with time.

The threshold of 0.781 for step 6 above was determined as follows:
1. A series of waveforms containing pacemaker pulses with varying amplitudes and widths of overshoot but without QRS complexes were input to the system.
2. The value 'R' (described in step 6) was computed for all the waveforms.
3. The threshold is set slightly higher than the largest value of 'R'.

This process ensures that overshoots without QRS complexes are never rejected as overshoots.

Figure 6:
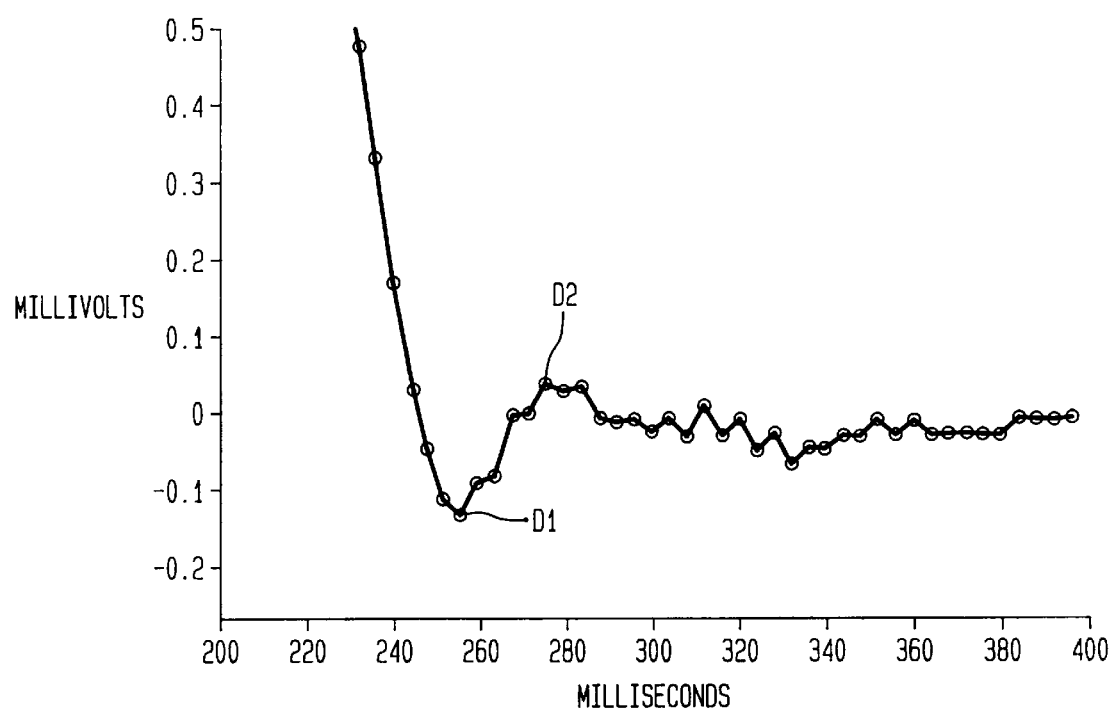
FIG. 6 illusrates an enlargment of the examplary waveform shown in FIG. 4.

Find post-pacer QRS step 214 decides if a QRS is present following a pacemaker pulse by performing the following operations on the filtered ECG data. Referring to FIG. 6, which shows an enlargement of a pacemaker overshoot having an associated QRS:
1. Locate the point 'D1' by searching for a point later in time than 'P2' (shown in FIG. 4) which is a peak. A peak is defined as a sample whose following sample is larger in amplitude if the amplitude at 'P2' was positively signed, or as the sample whose following amplitude is smaller in amplitude if the amplitude at 'P1' was negatively signed.
2. If the point 'D1' is not found by the aforementioned method, then a QRS is not detected.
3. If the point 'D1' is found, search forward in time from 'D1' for a point 'D2'. Point 'D2' is found at the end of a time period of 16 or more milliseconds during which no peak is found. A peak is defined as a sample whose following sample is larger in amplitude if the amplitude at 'D1' is positively signed, or as the sample whose following amplitude is smaller in amplitude if the amplitude at 'D1' is negatively signed.
4. If the point 'D2' is not found by the aforementioned method, then a QRS is not detected.
5. If the points 'D1' and 'D2' are both found, then the following computation is made:

$$A = |ECG_{D2} - ECG_{D1}|$$

A is the absolute value of the difference of sample voltage at 'D2' minus the sample voltage at 'D1'. If A exceeds 0.065 mV, then a QRS is detected; otherwise, a QRS is not detected.

The 0.065 mV threshold was determined as follows:
1. A series of waveforms containing overshoots and 0.35 mV QRS complexes buried in the overshoot were input to the system.
2. The value 'A'(described in step 5 above) was computed for all the waveforms.
3. The threshold is set slightly lower than the smallest value of 'A'.

This process ensures that QRS complexes of 0.35 mV or greater will be detected.

Figure 7:
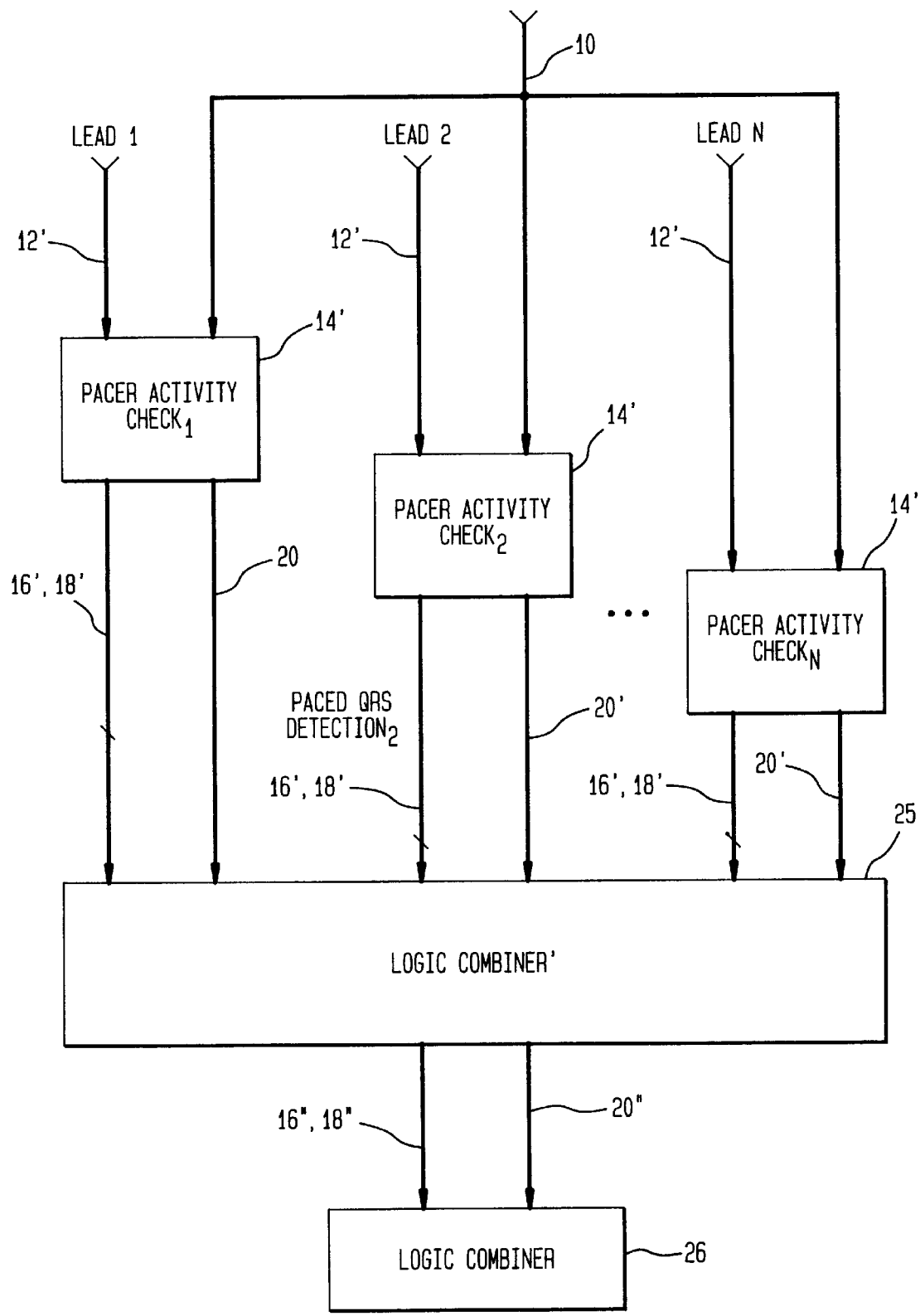
FIG. 7 illustrates in block diagram form a modification of a heart rate monitor constructed in accordance with an alternative embodiment of the present invention for processing multiple ECG signals.

In accordance with a further aspect of the present invention, the pacer activity detection technique described above can be extended so as to operate on multiple ECG signal leads (such as 2–12), thereby further increasing the sensitivity of paced QRS detection. Referring to FIG. 7:
1. A common pulse detection signal 10 developed by sensing a pacemaker pulse on any of a plurality of the ECG signals that are sensed, is applied in parallel to a plurality of pacer activity checkers 14', along with a respective plurality of corresponding ECG signals 12', one for each electrode 4 coupled to the patient 2.
2. Paced QRS detection outputs 16' and 18', and an overshoot detection output 20' output from each of the plurality of pacer activity checkers 14', corresponding substantially with paced QRS detection outputs 16 and 18 and the overshoot detection output 20 previously described, are input to an interim logic combiner 25.
3. Interim logic combiner 25 produces as outputs a combined pacer QRS detection signal 16" and 18" and a combined overshoot detection signal 20". One possible algorithm useful for logic combiner 25, but clearly not the only one, is to perform a logical OR operation on the paced QRS detection signals 16' and 18', to produce the combined pacer QRS detection signal 16" and 18", and to perform a logical AND operation on the overshoot detection signal 20' to produce a combined overshoot detection signal 20". The outputs 16", 18" and 20" would then be applied to logic combiner 26 for processing in the same manner that output signals 16, 18 and 20 were processed.

Thus, what has been shown and described is a paced QRS complex detector that fulfills all the objects and advantages sought therefore. Many changes, modifications, variations and other uses and applications of the subject invention will, however, become apparent to those skilled in the art after considering this specification and the accompanying drawings which disclose a preferred embodiment thereof. For example, monitor 6 to only be a real-time continuous patient monitor, but may also comprise a discontinuous type of heart rate monitor, such as a stress tester, Holter monitor, etc. Furthermore, the thresholds used in the illustrated embodiment were for purposes of illustration in the preferred embodiment, and clearly other thresholds and techniques for detecting the occurrence of amplitude changes in an ECG signal could be used. Similarly, other techniques could be used to validate the existence of a pacemaker overshoot other than the specific technique illustrated herein of computing the value R, e.g., one could use template matching techniques. In this regard, one could find the post-pacer QRS using a technique different than calculating the difference A, e.g., one could use an energy collection technique. All such changes, modifications, variations and other uses and applications which do not depart from the spirit and scope of the invention are deemed to be covered by the invention which is limited only by the claims which follow.

What is claimed is:

1. A heartrate monitor including a QRS detector for detecting QRS complexes in the presence of pacemaker pulses, comprising:

a signal receiver adapted for being coupled to at least one sensor coupled to a medical patient, for providing an ECG signal and a pacemaker detection signal;

a pacemaker activity checker, responsive to said pacemaker detection signal and said ECG signal for providing first and second output signals, said first output signal indicating the occurrence of a QRS complex in the vicinity of the pacemaker detection signal, and the second output signal indicating the occurrence of an overshoot in the vicinity of the pacemaker detection signal;

an overshoot validator, responsive to said ECG signals and said second output signal for indicating the validity of the indicated overshoot;

a QRS detector, responsive to said ECG signal, for indicating the occurrence of a QRS complex in said ECG signal;

a logic combining means, responsive to at least said first output signal, the output of said overshoot validator and the output of said QRS detector, for determining a combined QRS detection signal; and heartrate determining means responsive to said combined QRS detection signal for indicating a heartrate for the medical patient.

2. Apparatus in accordance with claim 1, wherein a differentiating filter is provided for filtering said ECG signals before they are applied to said pacer activity checker, and slope detection techniques are used to detect said QRS complexes and pacemaker pulses.

3. Apparatus in accordance with claim 1, wherein said logic combining means operates in accordance with the following table:

| Second signal | First signal | Action on QRS's from QRS Detector |
|---|---|---|
| True | False | Inhibit QRS |
| True | False | Count QRS as paced QRS if dual-chamber |
| False | False | Count QRS as paced QRS if dual-chamber |
| True | True | Count QRS as paced QRS |
| False | True | Count QRS as non-paced QRS |
| False | False | Count QRS as non-paced QRS |

4. Apparatus in accordance with claim 1, wherein said pacemaker activity checker provides as said first output signals an indication of the occurrence of a QRS complex that follows the pacemaker detection signal, and a third output signal indicating the occurrence of a QRS complex that preceeds the pacemaker detection signal.

5. Apparatus in accordance with claim 4, wherein said logic combining means operates in accordance with the following table:

| Second signal | Third signal | First signal | Action on QRS's from QRS Detector |
|---|---|---|---|
| True | False | False | Inhibit QRS |
| True | True | False | Count QRS as paced QRS if dual-chamber |
| False | True | False | Count QRS as paced QRS if dual-chamber |
| True | False | True | Count QRS as paced QRS |
| False | False | True | Count QRS as non-paced QRS |
| False | False | False | Count QRS as non-paced QRS |

6. A method for operating a QRS detector for detecting QRS complexes in the presence of pacemaker pulses, comprising the following steps:

processing an ECG signal so as to develop a pacemaker pulse detection signal;

processing said ECG signal so as to develop first and second output signals indicating signal activity in the vicinity of detected pacemaker pulses, said first output signal indicating the occurrence of a QRS complex in the vicinity of the pacemaker detection signal, and the second output signal indicating the occurrence of an overshoot in the vicinity of the pacemaker detection signal;

validating said second output signal for indicating the validity of the indicated overshoot;

indicating the occurrence of a QRS complex in said ECG signal;

processing said first and second output signals and the indication of a QRS complex, for determining a combined QRS detection signal; and determining a heartrate in responsive to said combined QRS detection signal.

* * * * *

UNITED STATES PATENT AND TRADEMARK OFFICE
CERTIFICATE OF CORRECTION

PATENT NO. : 5,771,898
DATED : June 30, 1998
INVENTOR(S) : Janet Tamada

It is certified that error appears in the above-identified patent and that said Letters Patent is hereby corrected as shown below:

In column 16, line 41, "blood substance levels." should be -- blood substance level. --;
    line 43, "calculating substance" should be -- calculating a substance --;
    line 55, delete "10 minutes to about 1 cycle per hour."

Signed and Sealed this

Twenty-seventh Day of February, 2001

*Attest:*

NICHOLAS P. GODICI

*Attesting Officer*      Acting Director of the United States Patent and Trademark Office

UNITED STATES PATENT AND TRADEMARK OFFICE
CERTIFICATE OF CORRECTION

PATENT NO. : 5,771,898
DATED : June 30, 1998
INVENTOR(S) : Stephen A. Marinello

It is certified that error appears in the above-identified patent and that said Letters Patent is hereby corrected as shown below:

This certificate supercedes certificate of correction issued February 27, 2001, the number was erroneously mentioned and should be deleted since no Certificate of Correction was granted.

Signed and Sealed this

Eleventh Day of September, 2001

*Attest:*

*Attesting Officer*

NICHOLAS P. GODICI
*Acting Director of the United States Patent and Trademark Office*